(12) United States Patent
Kahlman et al.

(10) Patent No.: US 9,250,181 B2
(45) Date of Patent: Feb. 2, 2016

(54) SENSOR DEVICE WITH IMAGING OPTICS

(75) Inventors: Josephus Arnoldus Henricus Maria Kahlman, Tilburg (NL); Joannes Baptist Adrianus Dionisius Van Zon, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 803 days.

(21) Appl. No.: 13/498,347

(22) PCT Filed: Sep. 27, 2010

(86) PCT No.: PCT/IB2010/054328
§ 371 (c)(1),
(2), (4) Date: May 30, 2012

(87) PCT Pub. No.: WO2011/036650
PCT Pub. Date: Mar. 31, 2011

(65) Prior Publication Data
US 2012/0262565 A1 Oct. 18, 2012

(30) Foreign Application Priority Data
Sep. 28, 2009 (EP) .................................. 09171479

(51) Int. Cl.
| H04N 13/00 | (2006.01) |
| G01N 21/55 | (2014.01) |
| G01N 27/00 | (2006.01) |
| G01N 21/00 | (2006.01) |
| G01J 1/58 | (2006.01) |
| G01N 21/552 | (2014.01) |
| G01N 21/64 | (2006.01) |
| G02B 21/36 | (2006.01) |

(52) U.S. Cl.
CPC ............ *G01N 21/552* (2013.01); *G01N 21/648* (2013.01); *G02B 21/367* (2013.01)

(58) Field of Classification Search
CPC ............................ G02B 21/365; G02B 21/367
USPC ................ 348/79; 436/150; 422/82.01, 82.05
See application file for complete search history.

(56) References Cited

U.S. PATENT DOCUMENTS

| 7,018,838 B2 | 3/2006 | Murphy |
| 2009/0057147 A1 | 3/2009 | Kayyem |

(Continued)

FOREIGN PATENT DOCUMENTS

| EP | 1235424 A2 | 8/2002 |
| WO | 0059206 A1 | 10/2000 |

(Continued)

OTHER PUBLICATIONS

Printed Publication: Yuk J. S. et al: "Development of a scanning surface plasmon microscope based on white light for analysis of a wide range of protein arrays", Sensors and Actuators B, vol. 131. No. 1, Apr. 14, 2008, pp. 241-246, XP022602890, Elseivier Sequoia S.A., Lausanne, CH, ISSN: 0925-4005, DOI: 10.1016/J.SNB.2007.11.019.*

(Continued)

*Primary Examiner* — Sath V Perungavoor
*Assistant Examiner* — Patricia I Young

(57) ABSTRACT

The invention relates to a method and a sensor device (100) for detecting particles (MP) that are bound to the binding surface (12) of a carrier (11). The sensor device (100) comprises a microscope (50) for imaging bound particles (MP) onto an image sensor (53). In order to increase the spatial resolution of the microscope (50), a displacement unit (60, 70, 80) is provided that can displace the carrier (11) relative to the image sensor (53). The distance of a bound particle (MP) from the binding surface (12) and/or its lateral displacement in reaction to forces can thus be determine with high accuracy. This allows to discriminate specific bindings of large magnetic particles (MP) that are bound to the binding surface (12) via smaller target particles from nonspecific direct bindings.

18 Claims, 2 Drawing Sheets

(56) References Cited

U.S. PATENT DOCUMENTS

2009/0186420 A1* 7/2009 Kahlman et al. .............. 436/150
2009/0242798 A1* 10/2009 Bewersdorf et al. ....... 250/458.1

FOREIGN PATENT DOCUMENTS

| WO | 2008021071 A2 | 2/2008 |
| WO | 2008142492 A1 | 11/2008 |
| WO | 2008155716 A1 | 12/2008 |
| WO | 2009001276 A1 | 12/2008 |

OTHER PUBLICATIONS

Yuk, Jong Seol et al "Development of a Scanning Surface Plasmon Microscope based on White Light for Analysis of a Wide Range of Protein Arrays" Sciencedirect Sensors and Actuators B, vol. 131, 2008, pp. 241-246.

Watanabe, Kouyou et al "Localized Surface Plasmon Microscope with an Illumination System Employing a Radially Polarized Zeroth-Order Bessel Beam" Optics Letters, vol. 34, No. 8, Apr. 15, 2009, pp. 1180-1182.

* cited by examiner

SENSOR DEVICE WITH IMAGING OPTICS

FIELD OF THE INVENTION

The invention relates to a sensor device and a method for detecting particles that are bound to a binding surface of a carrier.

BACKGROUND OF THE INVENTION

The WO 2008/155716 discloses an optical biosensor in which an input light beam is totally internally reflected and the resulting output light beam is detected and evaluated with respect to the amount of target components at the reflection surface. The target components comprise magnetic particles as labels, which allows to affect the processes in the sample by magnetic forces.

SUMMARY OF THE INVENTION

Based on this situation it was an object of the present invention to provide means for improving the accuracy of particle detection, particularly for low particle concentrations.

This object is achieved by a sensor device and a method for detecting with a sensor device, according to various embodiments disclosed in the claims.

According to its first aspect, the invention relates to a sensor device for detecting particles at the surface of a carrier, wherein said surface is called "binding surface" in the following because the considered particles will in many important applications be bound to this surface. The particles to be detected will typically comprise nano particles or micro particles that have some property (e.g. optical density, magnetic susceptibility, electrical charge, fluorescence, radioactivity, etc.) which can be detected. The carrier will preferably be made from a transparent material, for example glass or polystyrene, to allow the propagation of light of a given (particularly visible, ultraviolet (UV), and/or infrared (IR)) spectrum. The carrier may be a part of the sensor device or an independent component separate from the sensor device, for example realized by a disposable cartridge. The sensor device comprises the following components:

a) An optical system with an image sensor onto which particles (if present at the binding surface) are imaged. As the image of particles on the image sensor will typically be magnified, the optical system with the image sensor will in the following—without loss of generality—be briefly called "microscope". Preferably, the microscope will image the binding surface through the (transparent) carrier.

b) A "displacement unit" for controllably displacing the image sensor of the microscope relative to the carrier. This relative displacement preferably takes place in such a way that there is (only) a lateral shift of the image of a particle on the image sensor. Moreover, said shift is preferably less then one pixel on the image sensor.

c) An evaluation unit for evaluating images that were generated at different relative displacements of the carrier and the image sensor. The evaluation unit may be realized by dedicated electronic hardware, digital data processing hardware with associated software, or a mixture thereof.

According to a second aspect, the invention relates to a method for detecting with a sensor device particles at the binding surface of a carrier, particularly particles that are bound to said binding surface, said method comprising the following steps:

a) Imaging particles onto an image sensor of a microscope.

b) Displacing with a displacement unit the image sensor relative to the carrier.

c) Evaluating with an evaluation unit images that were generated at different relative displacements of carrier and image sensor.

The method may preferably be executed with a sensor device according to the first aspect of the invention. Both the method and the sensor device have as a common feature that they evaluate images of (e.g. bound) particles which were generated at different relative positions of carrier and image sensor. Hence it is possible to increase the spatial resolution that can be achieved with the image sensor because information from at least two images taken from different viewing angles can be combined. This in turn allows a more accurate determination of the kind of particle and/or of the type of its binding, which helps to increase the quantitative accuracy of the sensor device and the detection method.

In the following, preferred embodiments of the invention will be described that relate to both the sensor device and the method described above.

According to a first preferred embodiment, the image sensor of the microscope is pixelated, i.e. it comprises a plurality of single sensor elements ("pixels") that can individually be read out. Such a pixelated image sensor may for example be realized by a CCD or a CMOS image sensor as it is known from digital cameras. In a pixelated image sensor, the spatial resolution is quantized (and limited) by the pixel size. The relative displacement between carrier and image sensor brings about that different pixels of the image sensor will receive images of a particle, which allows to increase the spatial resolution by overcoming the limits imposed by the pixel size.

In the aforementioned embodiment, the dimensions of the pixels are preferably such that (with respect to particles of a given size and a given magnification of the microscope) the image of a particle at the binding surface covers between one and about 20, preferably between about three and about 9 pixels on the image sensor. In this case the spatial resolution with which the position of bound particles can be determined is severely limited by the pixilation of the image sensor, and the displacement approach of the invention can hence provide a significant improvement.

It should be noted that the displacement between the carrier and the image sensor is assumed to be relative. With respect to a stationary environment of the sensor device (e.g. the laboratory), such a relative displacement can be achieved by (i) moving the carrier while the image sensor remains stationary, (ii) moving the image sensor while the carrier remains stationary, or (iii) moving both the carrier and the image sensor with different displacements relative to the stationary environment. Accordingly, there are several possibilities how the displacement unit can exert its effect. In preferred embodiments, the displacement unit is designed such that it displaces either only the carrier, or only the microscope (with the image sensor), or only the image sensor (without the rest of the microscope) with respect to the residual components of the sensor device. If the carrier or the complete microscope are displaced, this displacement shall preferably be at least as large as one pixel if the image sensor is pixelated; if the image sensor is displaced, a displacement of less than one pixel suffices.

According to a further development of the invention, the sensor device comprises an actuator unit for exerting forces on particles at the binding surface in a direction that is parallel to the binding surface. The reaction of a particle to such forces, i.e. the extent of its lateral displacement, provides valuable information about the existence and type of a binding to the binding surface, which may for example be used to distinguish specific bindings (which are desired according to the purpose of an assay) from nonspecific bindings (which relate to background noise).

The aforementioned actuator unit may for example comprise a magnet for exerting magnetic forces on (magnetic) particles, an electrical field generator for generating electrical forces (on charged or polarizable particles), or an ultrasound probe for mechanically displacing particles. With the mentioned devices, well controllable forces can be exerted on particles.

The actuator unit is preferably further adapted to generate forces on particles in opposite directions. Hence the direction of exerted forces can be changed, which helps to neutralize possible hysteresis or biasing effects.

According to another preferred embodiment, the actuator unit and the displacement unit are synchronized. This means that there is a given functional relation between the timing of relative displacements between carrier and image sensor on the one side and the exertion of forces on particles on the other side. Preferably, the synchronization is such that at least two images with different relative displacements between carrier and image sensor are generated for the same force generated by the actuator unit (hence imaging a bound particle with the same lateral displacement). Moreover, another pair of images taken at different displacements between carrier and image sensor should be generated for another value of the force exerted by the actuator unit on the (bound) particle. Hence the reaction of a (bound) particle to lateral forces can be determined with high spatial resolution.

The evaluation unit is preferably adapted to determine a parameter that is related to the distance between a particle and the binding surface, to the lateral displacement of a particle relative to a reference position on the binding surface, and/or to the residence time of a bound particle at the binding surface (i.e. the lifetime of a binding). The mentioned values comprise valuable information about the existence and type of a binding between a particle and the binding surface. In particular, the determined parameter can be used to discriminate between specific bindings one is interested in and nonspecific bindings.

According to another embodiment, the evaluation unit is adapted to select an isolated (e.g. bound) particle for evaluation. Isolation of a particle means that neighboring particles are at least a given minimal distance away (e.g. at least one or a few particle diameters). This requirement ensures that the considered particle is not affected by interactions with other particles.

In general, the sensor device and the method may be applied with many different types of particles and bindings of such particles to the binding surface. In a preferred application, the considered particle is a label particle, i.e. a particle which is used to label a target particle of another type one is actually interested in. Moreover, binding between said label particle and the binding surface shall take place specifically via a smaller target particle. The target particle may for example be a (small) molecule like a protein or nucleic acid, and the label particle may be a magnetic bead. In a typical example of such a system, the size of the target particle is in the order of 5 nm, while the label particle (magnetic bead) has a diameter of about 500 nm. Hence the geometrical difference between nonspecific direct binding of a label particle to the binding surface and a specific binding via a (small) target particle is quite small, but it can nevertheless be detected with the approach of the present invention.

The sensor device may optionally comprise a light source, for example a laser or an LED, for illuminating the binding surface with an evanescent wave. Such an evanescent wave may particularly be generated with an input light beam that is totally internally reflected at the binding surface. Illumination with an evanescent wave has the advantage that only a limited small volume immediately adjacent to the binding surface is affected while background noise from the bulk medium further away from the binding surface is suppressed.

According to another embodiment, the sensor device comprises a light source and a light detector for detecting particles at the binding surface with the help of a totally internally reflected light beam. In this setup of a frustrated total internal reflection, the amount of light that is missing in an output light beam due to scattering of evanescent waves during total internal reflection is used as an indication of the amount of particles at the reflection surface.

The invention further relates to the use of the microelectronic device described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which.

Like reference numbers in the Figures refer to identical or similar components.

DESCRIPTION OF PREFERRED EMBODIMENTS

Though the present invention will in the following be described with respect to a particular setup (using magnetic particles and frustrated total internal reflection as measurement principle), it is not limited to such an approach and can favorably be used in many different applications and setups.

Figure 1:
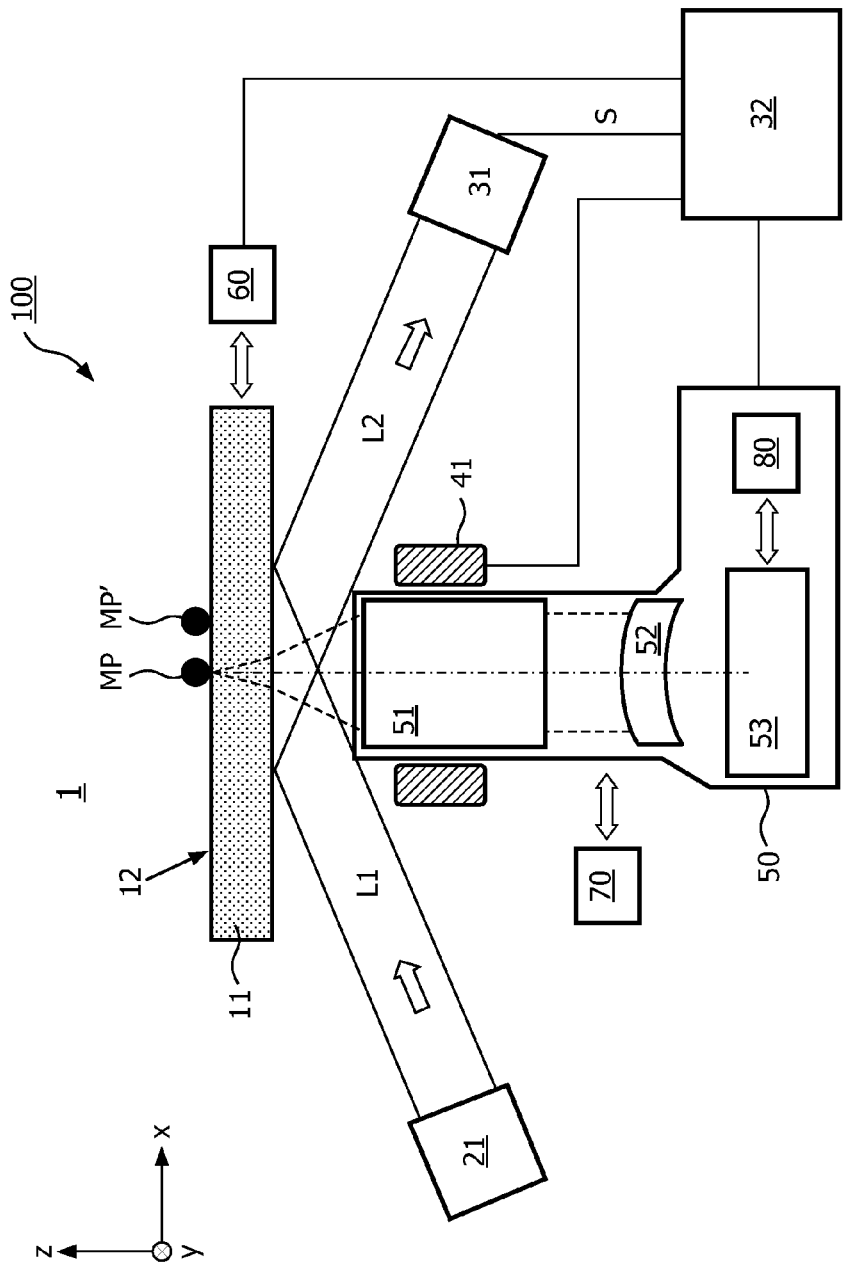
FIG. 1 schematically shows a sensor device according to the present invention.

FIG. 1 shows an exemplary setup (not to scale) with a sensor device 100 according to the present invention. One component of this setup is a carrier 11 that may for example be made from glass or transparent plastic like polystyrene. The carrier 11 is located next to a sample chamber 1 in which a sample fluid with target components to be detected (e.g. drugs, antibodies, DNA, etc.) can be provided. The sample further comprises magnetic particles, for example superparamagnetic beads, wherein these particles are usually bound (via e.g. a coating with antibodies) as labels to the aforementioned target components. The magnetic particles may bind in various ways to the sensor surface, for example "specifically" via a target particle and an antibody on the surface, or directly ("non-specifically"), e.g. with more than one bond which reduces the lateral movement. In the Figures, magnetic particles that are specifically bound via a target particle will have the reference sign MP, while magnetic particles non-specifically bond without a target particle will be denoted with MP'. It should be noted that instead of magnetic particles other label particles, for example electrically charged or fluorescent particles, could be used as well.

The interface between the carrier 11 and the sample chamber 1 is formed by a surface called "binding surface" 12. This binding surface 12 is coated with capture elements, e.g. antibodies Ab (cf. FIGS. 2, 3), which can specifically bind to target particles.

The sensor device 100 comprises a magnetic field generator 41, for example an electromagnet with a coil and a core, for controllably generating a magnetic field at the binding surface 12 and in the adjacent space of the sample chamber 1. With the help of this magnetic field, the magnetic particles MP, MP' can be manipulated, i.e. be magnetized and particularly be moved (if magnetic fields with gradients are used). Thus it is for example possible to attract magnetic particles MP, MP' to the binding surface 12 in order to accelerate their binding to said surface, or to wash unbound magnetic particles away from the binding surface before a measurement.

The sensor device 100 further comprises a light source 21 that generates an input light beam L1 which is transmitted into the carrier 11 through an "entrance window" (not shown). As light source 21, e.g. a commercial compact disc (CD) ($\lambda$=780 nm), digital video disc (DVD) ($\lambda$=658 nm), or blu-ray disc (BD) ($\lambda$=405 nm) laser-diode as well a high power ($\lambda$=650 nm) light emitting diode (LED) can be used. A collimator lens may be used to make the input light beam L1 parallel, and a pinhole may be used to reduce the beam diameter. The input light beam L1 arrives at the binding surface 12 at an angle larger than the critical angle of total internal reflection (TIR) and is therefore totally internally reflected in an "output light beam" L2. The output light beam L2 leaves the carrier 11 through another surface ("exit window", not shown) and is detected by a light detector 31. The light detector 31 determines the amount of light of the output light beam L2 (e.g. expressed by the light intensity of this light beam in the whole spectrum or a certain part of the spectrum). The measured sensor signals S are evaluated and optionally monitored over an observation period by an evaluation and control module 32 that is coupled to the detector 31.

It is possible to use the detector 31 also for the sampling of fluorescence light emitted by fluorescent particles which were stimulated by the input light beam L1, wherein this fluorescence may for example spectrally be discriminated from reflected light L2. Though the following description concentrates on the measurement of reflected light, the principles discussed here can mutatis mutandis be applied to the detection of fluorescence, too.

The described microelectronic sensor device applies optical means for the detection of magnetic particles MP, MP'. For eliminating or at least minimizing the influence of background (e.g. of the sample fluid, such as saliva, blood, etc.), the detection technique should be surface-specific. As indicated above, this is achieved by using the principle of frustrated total internal reflection (FTIR). This principle is based on the fact that an evanescent wave penetrates (exponentially dropping in intensity) into the sample chamber 1 when the incident light beam L1 is totally internally reflected. If this evanescent wave then interacts with another medium like the bound magnetic particles MP, MP', part of the input light will be coupled into the sample fluid (this is called "frustrated total internal reflection"), and the reflected intensity will be reduced (while the reflected intensity will be 100% for a clean interface and no interaction). Depending on the amount of disturbance, i.e. the amount of magnetic particles on or very near (within about 200 nm) to the TIR surface (not in the rest of the sample chamber 1), the reflected intensity will drop accordingly. This intensity drop is a direct measure for the amount of bound magnetic particles MP, MP', and therefore for the concentration of magnetic particles in the sample. The described procedure is independent of applied magnetic fields. This allows real-time optical monitoring of preparation, measurement and washing steps. The monitored signals can also be used to control the measurement or the individual process steps.

More details about the FTIR measurement principle may for example be found in the WO 2008/155716, WO 2009/001276 A1, and WO 2008/142492 A1.

The described sensor device 100 or similar biosensors can for example be applied for the detection of DNA (molecular diagnostics) and proteins (immuno-assays), both important markers for all kind of diseases in the human body. As described above, the immuno-assay techniques may use the specific coupling of small (super)paramagnetic particles or beads to a binding surface for the final optical detection (FTIR) of the biological markers. Based on this platform detection instruments are being developed for decentralized measurements such as the roadside testing of Drugs-Of-Abuse in saliva or the Point-Of-Care testing of cardiac markers in human blood at the physicians place. The concentrations of biological markers in Drugs-Of-Abuse testing are relatively large (nano-molar region) while the concentrations required for cardiac marker testing are already much lower (pico-molar region). For future applications even lower concentrations (femto-molar region) have to be detected, widening the range of diseases which can be detected. More sensitive detection techniques also allow quicker measurement times for the higher concentration regions.

The measurement of the mentioned low concentrations is currently only possible in centralized labs where extensive systems are used and the measurement times are long. It would therefore be desirable to have a system which can be operated in a decentralized setting while still having a centralized lab performance. The main challenges in such a system are a) how to increase the sensitivity of the system and b) how to discriminate between the signal of the specific biological marker to be tested and the inevitable background signal caused by non-specific binding.

The magnetic sensor device 100 described above typically uses magnetic beads with sizes between 200 nm and 1000 nm as labels. Since small magnetic beads cannot be attracted to the surface fast enough due to their limited magnetic content and large magnetic beads exhibit slower binding kinetics, most of the assay development is carried out with 500 nm beads. This size is hence used as an example in the remainder of this disclosure.

Figure 2:
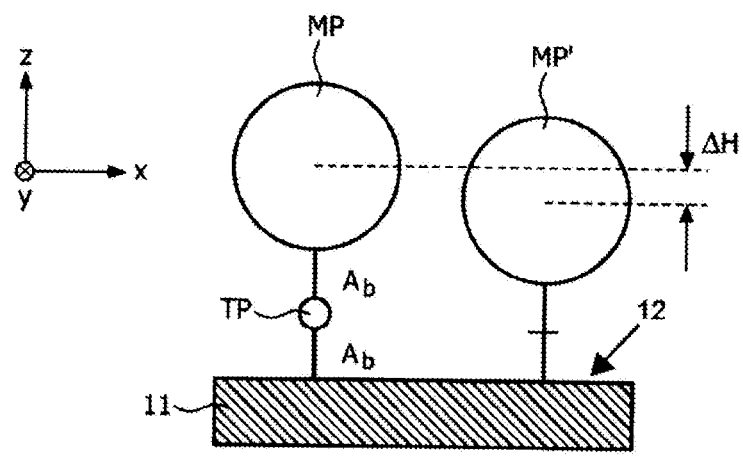
FIG. 2 illustrates the difference between specific and nonspecific bindings in a direction perpendicular to the binding surface.
Figure 3:
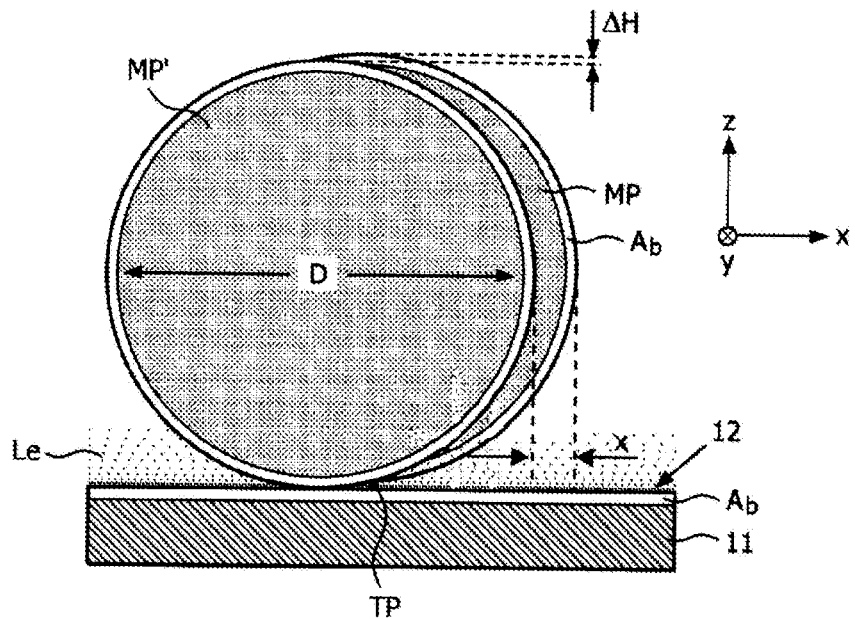
FIG. 3 illustrates the difference between specific and nonspecific bindings in a direction parallel to the binding surface.

In general, specific bonds of magnetic particles MP deviate from non-specific bonds of magnetic particles MP' in a number of ways, which are illustrated in FIG. 2 and FIG. 3:

a) In a specific bond the target molecule is always involved. This is illustrated in FIG. 2 (not to scale), where a magnetic particle MP is shown on the left that is specifically bound via an intermediate target particle (molecule) TP which binds to antibodies Ab on the magnetic particle's surface and on the binding surface 12 of the carrier 11, respectively. On the right side of FIG. 2, a non-specifically bound magnetic particle MP' is shown for which the antibodies Ab are directly coupled. Because of the finite size of the target particle TP, which might be several nanometers large (e.g. 5 nm), the distance between the bead and the binding surface 12 is an amount H larger for the specific bond than for the non-specific bond.

b) At low target concentrations there is only one target particle TP per bead on beads which are able to capture a target. Most of the beads do not capture a target particle. The beads containing a target particle have more chance to make a single, specific bond to the binding surface due to the higher association constant of a specific binding compared to a non-specific binding. Non-specific bonds have a much larger chance to make multiple bonds. The difference between a single bond and a multiple bond is visible in the lateral displacement, either caused by the thermal or Brownian motion or by lateral force. This is illustrated in FIG. 3 (which is drawn to scale). A bead MP of diameter D=500 nm with an antibody layer Ab with a thickness of 15 nm is attached to a binding surface 12, also comprising an antibody layer Ab with a thickness of 15 nm, by means of a 5 nm target particle TP. When the bead MP is displaced by means of a lateral force (in x, y-direction), it may be brought into direct contact with the binding surface 12, corresponding to the situation of the shown non-specifically bound bead MP'. The corresponding change in vertical position is H=5 nm while the change x in lateral direction (within the mean extension of an evanescent wave Le) is about 50 nm, i.e. ten times larger. Characteristic displacements which have to be measured are therefore in this range. By moving the bead MP from the maximum left position to the maximum right position the total displacement is twice as large.

c) Due to an exact fit of the geometrical shape of the target molecule TP and the capturing molecule (e.g. antibody Ab), a specific bond often involves more atomic interactions than a non-specific bond. A single specific bond is therefore often stronger than a single non-specific bond. This is reflected in a larger average residence time of the bead MP on the binding surface (i.e. a lower dissociation constant $k_{off}$).

In view of the above facts, it would be desirable to look in detail to each bond in terms of bond length (z), freedom of movement or displacement in lateral direction (x,y), and residence time on the surface (bond strength). This leads to the idea of adding an extra imaging system to the FTIR read-out by putting an objective lens close to the binding surface and projecting the image on a camera.

FIG. 1 illustrates this for the FTIR sensor device 100, which is additionally equipped with a microscope 50 comprising an objective lens 51, further lenses 52, and a camera or image sensor 53 (e.g. a CCD or CMOS chip).

In existing sensor devices, the above approach faces however the problem that the objective lens has to fit between the pole tips of a "horse-shoe" electromagnet. Since the distance between these pole tips is restricted to 1.5 mm due to performance requirements of the electromagnet, the available room for the light cone of the objective lens is strongly limited. Due to the limited room for the light cone of the objective lens, the spatial precision or resolution of such an imaging system would be inadequate to observe characteristic displacements of single 500 nm beads. This is caused by the fact that there is only room for a NA=0.4 objective lens, which limits the RMS (FWHM-spot) optical resolution to 1.3 µm at 20-fold magnification. As a result bead sizes on the camera sensor are enlarged to 1.3 µm×20=26 µm, which compares to 6×6 pixels on a 4.4×4.4 µm pixels of a high-end CMOS camera.

As mentioned above, specific and non-specific bonds can be discriminated on the basis of their bond length. Because the magnetic beads are illuminated by an exponential decaying evanescent field Le, their optical image is the convolution of the beads and the spatial optical transfer function, so that dispersion in the binding-height (z) and the bead diameter (D) will both change the observed light intensity I(z,D). That is why (x,y,z) bead-displacement is needed for unambiguous determination of said parameters.

When assuming a length of 5 nm of the typical target particles TP and a bead diameter of D=500 nm, the bead-displacements are typically 50 nm, which compares to a quarter of a pixel at 20 times magnification. Even when using a 6-pixel curve-fitting step to reconstruct the centre of mass, this is far too inaccurate for the intended application.

It is therefore proposed here to (1) vary the position of the imaging system with respect to the cartridge surface, (2) take a camera picture of at least two positions, and (3) combine said pictures to retrieve more spatial resolution.

Returning to FIG. 1, the aforementioned general principle is illustrated with respect to a specific embodiment. As already mentioned, the sensor device 100 features an additional microscope 50 for imaging magnetic particles MP, MP', which are (specifically or non-specifically) bound to the binding surface 12 of the carrier 11, onto the plane of the image sensor 53. In order to realize a relative displacement between the carrier 11 and the image sensor 53, a displacement unit can be inserted at different positions. In FIG. 1, three possibilities are shown in parallel for purposes of illustration (a real sensor device would of course usually realize only one of them):

The first type of displacement unit 60 is coupled to the carrier 11 in order to controllably move this in x- or y-direction while the rest of the setup remains stationary.

A second type of displacement unit 70 is coupled to the whole microscope 50 for controllably displacing this in x- or y-direction with respect to the stationary environment.

Finally, a third type of displacement unit 80 is integrated into the microscope 50. It can controllably displace only the image sensor 53 relative to the stationary environment and relative to the rest of the microscope 50.

The displacement units 60, 70, 80 are preferably connected to the evaluation and control unit 32 which controls their operation. They may in practice be realized in different ways, for example with piezo elements, a motor driven sledge or the like.

With the described microscope 50 and the displacement units 60 or 70, bindings can be observed from different viewing-positions (position, angle) by using mechanical actuation of the binding surface 12 or the total imaging system 50. By combining camera-frames, it is possible to improve the optical resolution of the total optical system and limit the quantization effects of the limited pixel size. Preferably the displacement of the bead image on the image sensor 53 comprises in these setups less than one camera pixel.

A (lateral) displacement of the beads MP MP' relative to the binding surface 12 can be introduced by a rather constant or varying magnetic, electrical or mechanical (e.g. ultra sound) force applied to said beads. Magnetic forces could for example be exerted with the magnet 41 or a further magnet (not shown). Camera frames can then be taken preferably synchronous to said force/displacement, wherein synchronization may be guaranteed by the evaluation and control unit 32. Displacement hysteresis effects can be suppressed by displacing the beads in opposite directions (both positive and negative).

In a variation on this theme, displacement of the carrier 11 by the displacement unit 60 may introduce both bead movement (driven by inertial forces) as well as displacement of viewing position.

As bead-bead interactions largely affect the resulting magnetic force, the signal processing algorithm preferably comprises the step of selecting isolated beads.

When only the relative position of the image sensor is displaced with the displacement unit 80, virtually more camera pixels are generated at the cost of lower effective framerate. Preferably the displacement comprises less than one camera pixel in this case. The required displacement of the image sensor is typically larger than about 25 nm and can be provided by commercially available piezo actuators.

The described approaches enable the combination of magnetic actuation, FTIR and microscopy by using a smaller sized objective lens. Hence the detection of 10-ths of nanometer bead movements becomes possible.

While the invention was described above with reference to particular embodiments, various modifications and extensions are possible, for example:

The sensor device can comprise any suitable sensor to detect the presence of particles on or near to a sensor surface, based on any property of the particles, e.g. it can detect via magnetic methods, optical methods (e.g. imaging, fluorescence, chemiluminescence, absorption, scattering, evanescent field techniques, surface plasmon resonance, Raman, etc.), sonic detection (e.g. surface acoustic wave, bulk acoustic wave, cantilever, quartz crystal etc), electrical detection (e.g. conduction, impedance, amperometric, redox cycling), combinations thereof, etc. A magnetic sensor can particularly comprise a coil, magneto-resistive sensor, magneto-restrictive sensor, Hall sensor, planar Hall sensor, flux gate sensor, SQUID, magnetic resonance sensor, etc.

In addition to molecular assays, also larger moieties can be detected with sensor devices according to the invention, e.g. cells, viruses, or fractions of cells or viruses, tissue extract, etc.

The detection can occur with or without scanning of the sensor device with respect to the sensor surface.

Measurement data can be derived as an end-point measurement, as well as by recording signals kinetically or intermittently.

The particles serving as labels can be detected directly by the sensing method. As well, the particles can be further processed prior to detection. An example of further processing is that materials are added or that the (bio)chemical or physical properties of the label are modified to facilitate detection.

The device and method can be used with several biochemical assay types, e.g. binding/unbinding assay, sandwich assay, competition assay, displacement assay, enzymatic assay, etc.

The device and method are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

With nano-particles are meant particles having at least one dimension ranging between 3 nm and 5000 nm, preferably between 10 nm and 3000 nm, more preferred between 50 nm and 1000 nm.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A sensor device for detecting label particles at the binding surface of a carrier, the sensor device comprising:
    a) a microscope with an image sensor onto which label particles are imaged, at least one label particle being bound to the binding surface of the carrier via a target particle;
    b) a displacement unit for controllably displacing the image sensor relative to the carrier; and
    c) an evaluation unit for evaluating images generated by the image sensor at different relative displacements of the carrier and the image sensor to identify the at least one label particle being bound to the binding surface of the carrier via the target particle, indicating presence of the target particle.

2. A method for detecting with a sensor device label particles at a binding surface of a carrier, the method comprising:
    a) imaging label particles at the binding surface of the carrier onto an image sensor of a microscope, one or more of the label particles being bound to the binding surface of the carrier via a corresponding target particle;
    b) displacing with a displacement unit the image sensor and the carrier relative to one another; and
    c) imaging the label particles bound at the binding surface the carrier onto the image sensor at a different relative displacement of the image sensor and the carrier, and
    d) evaluating with an evaluation unit images of the label particles generated at the different relative displacements of the carrier and the image sensor to identify the one or more label particles being bound to the binding surface of the carrier via the corresponding target particles, indicating presence of the target particles.

3. The sensor device according to claim 1, wherein the image sensor is pixelated.

4. The sensor device according to claim 3, wherein the image of each label particle covers between one and about 20 pixels on the image sensor.

5. The sensor device according to claim 1, wherein the displacement unit displaces at least one of the carrier, the microscope and the image sensor.

6. The sensor device according to claim 1, further comprising:
    an actuator unit for exerting forces on the label particles in a direction parallel to the binding surface, resulting lateral displacement of the label particles.

7. The sensor device according to claim 6, wherein the actuator unit comprises a magnet, an electrical field generator, or an ultrasound probe.

8. The sensor device according to claim 6, wherein the actuator unit is adapted to generate forces in opposite directions.

9. The sensor device according to claim 6, wherein the actuator unit and the displacement unit are synchronized.

10. The sensor device according to claim 6, wherein the evaluation unit is adapted to determine a parameter that is related to at least one of a distance of the label particles above the binding surface, the lateral displacement of the label particles, and a residence time of the bound label particles with respect to the binding surface.

11. The sensor device according to claim 1, wherein the evaluation unit is adapted to select an isolated label particle for evaluation.

12. The sensor device according to claim 1, wherein each of the labeled particles comprises a magnetic bead, which binds via the target particle to the binding surface.

13. The sensor device according to claim 1, further comprising:
a light source for illuminating the binding surface with an evanescent wave.

14. The sensor device according to claim 1, further comprising:
a light source and a light detector for detecting the label particles with a totally internally reflected light beam.

15. The sensor device according to claim 1, wherein the image of each label particle covers between about 3 and about 9 pixels on the image sensor.

16. The method according to claim 2, wherein evaluating the images generated at the different relative displacements of the carrier and the image sensor further enables more accurate determination of types of binding of the label particles bound at the binding surface of the carrier.

17. The method according to claim 2, wherein the image sensor is pixelized, and imaging the label particles bound at the binding surface the carrier onto the image sensor at the different relative displacement of the image sensor and the carrier causes different pixels of the image sensor will receive images of a target particle, overcoming limits on special resolution imposed by pixel size.

18. A method for detecting with a sensor device label particles at a binding surface of a carrier, the method comprising:
imaging the label particles at a binding surface of the carrier using an image sensor of a microscope, one or more of the label particles being bound to the binding surface of the carrier via a corresponding target particle;
displacing the label particles in a direction parallel to the binding surface;
imaging the displaced label particles; and
evaluating images of the label particles and the displaced label particles to identify each label particle being bound to the binding surface of the carrier via the corresponding target particle to determine presence of each corresponding target particle.

* * * * *